(12) United States Patent
Soloviev

(10) Patent No.: US 12,008,705 B2
(45) Date of Patent: Jun. 11, 2024

(54) X-RAY TOMOGRAPHY SYSTEM AND METHOD

(71) Applicant: ADAPTIX LTD, Begbroke (GB)

(72) Inventor: Vadim Soloviev, Begbroke (GB)

(73) Assignee: ADAPTIX LTD, Begbroke (GB)

( * ) Notice: Subject to any disclaimer, the term of this patent is extended or adjusted under 35 U.S.C. 154(b) by 271 days.

(21) Appl. No.: 17/672,601

(22) Filed: Feb. 15, 2022

(65) Prior Publication Data

US 2022/0172425 A1    Jun. 2, 2022

Related U.S. Application Data

(63) Continuation of application No. PCT/IB2020/057673, filed on Aug. 14, 2020.

(30) Foreign Application Priority Data

Aug. 16, 2019  (GB) ..................................... 1911759
Dec. 19, 2019  (GB) ..................................... 1918798

(51) Int. Cl.
  *G06T 15/08*  (2011.01)
  *G06T 7/00*   (2017.01)

(52) U.S. Cl.
  CPC ............ *G06T 15/08* (2013.01); *G06T 7/0012* (2013.01); *G06T 2207/10076* (2013.01)

(58) Field of Classification Search
  CPC .............................. G06T 15/08; G06T 7/0012
  See application file for complete search history.

(56) References Cited

U.S. PATENT DOCUMENTS

| 5,838,756 A | 11/1998 | Taguchi et al. |
| 2005/0041781 A1 | 2/2005 | Jefferson |
| 2007/0140408 A1 | 6/2007 | Takiura et al. |

(Continued)

FOREIGN PATENT DOCUMENTS

| JP | H09187450 | 7/1997 |
| JP | 2005-522304 | 7/2005 |

(Continued)

OTHER PUBLICATIONS

UKIPO, Search Report in corresponding GB application GB1911759.7, Feb. 21, 2020.

(Continued)

*Primary Examiner* — Edward Park
(74) *Attorney, Agent, or Firm* — Alley IP

(57) ABSTRACT

The majority of image reconstruction algorithms are common to DT and CT, and require reconstruction volume allocation and are based on ray tracing techniques. Reconstructed three-dimensional images become available only after the entire volume is processed and the algorithm completes. The present invention performs reconstruction on a slice-by-slice basis, instead of waiting for completion of the algorithm by back-projecting each pixel in each attenuation image towards the emitter that generated that image, onto a selected reconstruction slice and determining a proportion of overlap with grid cells in the slice to obtain weighting factors in order to calculate an average back-projected intensity for each grid cell in the selected reconstruction slice.

2 Claims, 3 Drawing Sheets

(56) References Cited

U.S. PATENT DOCUMENTS

| | | | |
|---|---|---|---|
| 2011/0052022 A1* | 3/2011 | Xu | G06T 11/005 |
| | | | 378/4 |
| 2011/0141111 A1 | 6/2011 | Singh | |
| 2014/0153803 A1 | 6/2014 | Noda | |
| 2015/0228092 A1 | 8/2015 | Claus | |
| 2016/0015350 A1* | 1/2016 | Chang | A61B 6/032 |
| | | | 250/362 |
| 2016/0081645 A1 | 3/2016 | Fukuda | |
| 2017/0046858 A1 | 2/2017 | Brokish et al. | |
| 2019/0099146 A1 | 4/2019 | Mistretta et al. | |

FOREIGN PATENT DOCUMENTS

| | | |
|---|---|---|
| JP | 2007-151806 | 6/2007 |
| JP | 2010-115475 | 5/2010 |
| JP | 2012-010891 | 1/2012 |
| JP | 2014-023936 | 2/2014 |
| JP | 2014-128576 | 4/2018 |
| WO | 2016/111016 | 7/2016 |

OTHER PUBLICATIONS

WIPO, Report on Patentability in corresponding PCT application PCT/IB2020/057673, Oct. 12, 2021.
WIPO, International Search Report in corresponding PCT application PCT/IB2020/057673, Oct. 29, 2020.
JPO, Search Report in corresponding JP application 2022-510083, Mar. 29, 2024.

* cited by examiner

X-RAY TOMOGRAPHY SYSTEM AND METHOD

RELATED APPLICATIONS

This application claims the benefit under 35 U.S.C. § 120, and is a continuation, of co-pending International Application PCT/IB2020/057673, filed Aug. 14, 2020 and designating the US, which claims priority to GB Applications 1911759.7, filed Aug. 16, 2019, and 1918798.8, filed Dec. 19, 2019, such GB Applications also being claimed priority to under 35 U.S.C. § 119. These GB and International applications are incorporated by reference herein in their entireties.

FIELD

The present invention relates generally to a digital tomography and finds particular, although not exclusive, utility in x-ray tomography.

BACKGROUND

Digital Tomosynthesis (DT) is a type of limited angle tomography providing the benefits of 3D imaging. Much like Computerized Tomography (CT), DT allows greater detection of 3D structures by viewing one slice at a time. A high in-plane resolution, three-dimensionality and a low radiation dose make DT an attractive alternative to CT in many medical imaging applications.

In contrast to CT, the DT projection dataset is incomplete, which violates the tomographic sufficiency conditions and results in limited angle artefacts in the reconstructed images. Although DT is a volumetric imaging technique and provides information on an object's internal structure, the entire 3D information about the object cannot be reconstructed.

The majority of image reconstruction algorithms are common to DT and CT, and the most popular ones include simultaneous algebraic reconstruction, filtered back-projection, cone beam reconstruction, and their variants. The image reconstruction can also be formulated as solving an optimization problem. All of the aforementioned methods require reconstruction volume allocation and are based on ray tracing techniques. Reconstructed three-dimensional images become available only after the entire volume is processed and the algorithm completes.

SUMMARY

An emitter panel consisting of an array of small x-ray emitters rather than a single source is advantageous because no physical movement is required avoiding the cost of motorized movers, and avoiding motion blur by electronically switching between emitters.

According to the present invention, there is provided a method of producing a tomogram, the method comprising the steps of: providing an x-ray detector panel comprising a plurality of pixels; providing an x-ray emitter panel spaced from the x-ray detector panel, the emitter panel comprising a plurality of x-ray emitters; identifying relative locations of the emitters and pixels relative to each other; emitting a respective cone of x-ray radiation from each emitter toward the detector panel; producing respective attenuation images at the detector panel in response to each respective cone of x-ray radiation impinging the detector panel; and reconstructing a density function indicative of attenuation of the x-ray radiation by: selecting a reconstruction slice corresponding to a plane located between the detector and emitter panels; providing an array of grid cells on the reconstruction slice; in response to selecting the reconstruction slice: for each respective attenuation image, back-projecting each pixel in the respective attenuation image back towards the respective emitter for that attenuation image onto the reconstruction slice and determining a proportion of overlap of that back-projected pixel with each grid cell to obtain a plurality of weighting factors comprising a respective weighting factor for each grid cell for that back-projected pixel; using the plurality of weighting factors for each back-projected pixel in each attenuation image to calculate an average back-projected intensity for each grid cell in the selected reconstruction slice to produce an average intensity image for the selected reconstruction slice; and convolving the average intensity image with a ramp filter to obtain the density function within the selected reconstruction slice.

Accordingly, reconstruction may be performed on a slice-by-slice basis, where slices are taken in planes parallel to the first plane. One slice at a time may be reconstructed interactively instead of waiting for completion of the algorithm. This approach is much faster than previous methods, and is far less demanding on computer memory. This approach is especially efficient when only a part of the entire reconstruction volume is of interest.

The method may explicitly include the step of producing a tomogram from the reconstructed density function.

Surprisingly, the present invention allows higher contrast images to be produced, particularly for relatively thick objects being scanned.

Identifying relative locations of the emitters and pixels relative to each other may comprise receiving indications from hardware (e.g. firmware readouts), receiving position information from registration pins on the emitter and/or detector panels, receiving location information from positioning armatures or similar devices for manoeuvring the emitter and detector panels, receiving indications of relative orientations of the panels, etc.

The attenuation image may represent a radon transform of the spatial distribution of the transport coefficient (e.g. the Beer-Lambert law).

Selecting a reconstruction slice may comprise an operator choosing a slice, or the slice may be chosen automatically by a computer; for example, the choice of slice may be predefined.

Reconstructing a density function indicative of attenuation of the x-ray radiation may further comprise selecting a further reconstruction slice. The further reconstruction slice may be selected in a similar way, and reconstruction may be performed in a similar manner. In this way, an operator may view the first reconstruction slice, and determine on the basis of those results which reconstruction slice to select next. Alternatively, this further selection may be performed automatically (e.g. be predetermined). Subsequent selection of reconstruction slices may be performed in a similar manner until an entire region has been reconstructed.

The plane may be substantially flat; i.e. planar. The plane may be orientated parallel to the detector panel; however, in alternative embodiments, may be tilted (i.e. at any orientation) with respect to the detector panel. Similarly, the plane may be orientated parallel to the emitter panel or may be tilted with respect to the emitter panel.

Providing the array of grid cells on the reconstruction slice may be predetermined, chosen by an operator or may be calculated. The array of grid cells on each slice may be the same as on each other slice, alternatively or additionally, they may be different. Furthermore, the dimensions of the array of grid cells may differ to the dimensions of the array of pixels on the detector panel, such that the pixel size and number of pixels of the backprojected image may not match the pixel size and the number of pixels of the detector panel.

Providing the array of grid cells on the reconstruction slice may comprise orthographically projecting the plurality of pixels onto the reconstruction slice to obtain a two-dimensional array of corresponding grid cells.

Alternatively, providing the array of grid cells on the reconstruction slice may comprise orthographically projecting the plurality of emitters onto the reconstruction slice to obtain a two-dimensional array of corresponding grid cells. However, any other method of calculation may be employed, depending on the resolution of the reconstruction slice required and/or possible within the limits of the hardware.

The pixel value may be backprojected at the specified height of the plane along rays connecting the pixel's corners and the emitter, such that the pixels of the detector panel are mapped onto the reconstruction slice. This mapping may be achieved by firing an imaginary ray from each of the four corners of each pixel of the detector panel to a given emitter, such that the four rays form a pyramid. The intersection between the pyramid and the selected reconstruction slice may then define the orthographic projection. Because the dimensions of the array of grid cells may differ to the dimensions of the array of pixels on the detector panel, the orthographic projection may only cover a proportion of some grid cells.

Determining a proportion of overlap of that back-projected pixel with each grid cell may comprise determining, for each grid cell that the orthographic projection covers, the proportion of the grid cell covered by the orthographic projection, and then this area may be furthermore divided by the area of the grid cell, which results in the weighting factor.

The pixel value of the respective attenuation image is weighted by this factor and added to the value of the grid cell. This may be repeated for all attenuation images to get a composite value for the grid cell, which may then be normalized with respect to the total number of overlapping pixels in the reconstruction plane to get an average value.

Convolving the average intensity image with a ramp filter to obtain the density function within the selected reconstruction slice may comprise evaluating the reconstruction formula:

$$f(x,y) \approx \tfrac{1}{2} \{ \int dx' h(x-x') \langle \check{g}(x',y) \rangle + \int dy' h(y-y') \langle \check{g}(x,y') \rangle \}$$

in which:
  $f$ is the density function indicative of attenuation of the x-ray radiation;
  x, y are Cartesian co-ordinates in the reconstruction plane;
  x', y' are Cartesian parameters used in the integrals;
  $\langle \check{g} \rangle$ in an average intensity determined for the reconstruction plane; and
  h is a ramp filter.

The ramp filter may comprise any suitable ramp filter known in the art. For example, the ramp filter may be given by:

$$h(x-x') = \tfrac{1}{2} \int |k| e^{2\pi i k(x-x')} dk$$

where k is a wavenumber along the x-axis; and/or $$h(n) = \frac{1}{4} \frac{1}{(4\lambda)^2} \text{ for } n = 0,$$

$$h(n) = \frac{1}{(4\lambda)^2} \left\{ \frac{(-1)^{(n-1)/2}}{\pi n} - \frac{2}{(\pi n)^2} \right\} \text{ for odd } n$$

$$h(n) = \frac{1}{(4\lambda)^2} \frac{-2[1-(-1)^{n/2}]}{(\pi n)^2} \text{ for non-zero even } n$$

where n is the distance x or y in pixels, and $\lambda$ is a size of a pixel. $\lambda$ may be an analogue of the wavelength of the selected reconstruction grid being used.

The method may further comprise identifying a discontinuity in average intensity determined for the reconstruction plane $\langle \check{g} \rangle$, for example caused by flat panel detector boundaries. For example, this may be achieved by, for each grid cell, determining a number of attenuation images, the back projection of which contribute to that respective grid cell, and comparing respective numbers of attenuations images of adjacent grid cells. In response to identifying a different number of attenuation images, for instance, along the x-axis in adjacent grid cells, a contour of integration (e.g. a straight line) may be defined with the discontinuity at $x_c$ (where we have a jump), or along the y-axis with discontinuity at $y_c$. Other methods of defining $x_c$ and/or $y_c$ are also contemplated. Further discussion of contours will make reference to the x-axis only, though application to the y-axis as well is both possible and desirable (though not necessary) and may be applied in the same way.

Convolving the average intensity image with a ramp filter to obtain the density function within the selected reconstruction slice may comprise evaluating the reconstruction formula:

$$f(x,y) \approx \tfrac{1}{2} \{ \int dx' h(x-x') \check{\psi}(x',y) + \int dy' h(y-y') \langle \check{g}(x,y') \rangle \}$$

in which:
  $\check{\psi}(x', y)$ may be equal to $$\langle \check{g} \rangle - \text{sign}(x' - x_c) \langle \check{g} \rangle' \frac{1}{4\pi^2} \ln|x' - x_c|$$

when x' is close to $x_c$, and $\check{\psi}(x', y)$ may be equal to $\langle \check{g} \rangle$ when x' is far from $x_c$;

$\langle \check{g} \rangle'$ is the derivative of $\langle \check{g} \rangle$; and
  $\text{sign}(x-x_c)$ is the sign (plus or minus) of the expression $x-x_c$.

x being close to $x_c$ may mean being within a predetermined number of pixels, in particular between 3 and 30, more particularly between 5 and 25, for example between 10 and 20, e.g. 15.

x being far from $x_c$ may mean being outside of a predetermined number of pixels, in particular between 3 and 30, more particularly between 5 and 25, for example between 10 and 20, e.g. 15.

That is, average intensity determined for the reconstruction plane $\langle \check{g} \rangle$ is substituted with the function $\check{\psi}$ near to the contours. The above approach holds similarly for contours parallel to the x-axis (e.g. at $y_c$), and the substitution may be carried out in both integrals if contours parallel to both the x- and y-axes are to be corrected for.

In edge cases, one of the integrals may drop out (i.e. evaluate to zero), resulting in:

$$f(x,y) \approx \frac{1}{2} \{\int dx' h(x-x') \psi(x',y)\}$$

in the case of x, and a similar statement in the case of y, the necessary changes having been made.

According to a second aspect of the present invention, there is provided a system for producing a tomogram, the system comprising: an x-ray emitter panel comprising a plurality of x-ray emitters, each emitter configured to emit a respective cone of x-ray radiation; an x-ray detector panel comprising a plurality of pixels, the x-ray detector panel spaced from the x-ray emitter panel and configured to produce respective attenuation images in response to each respective cone of x-ray radiation impinging the detector panel from the x-ray emitter panel; a spatial location system for identifying relative locations of the emitters and pixels relative to each other; and a processor for reconstructing a density function indicative of attenuation of the x-ray radiation by: selecting a reconstruction slice corresponding to a plane located between the detector and emitter panels; providing an array of grid cells on the reconstruction slice; in response to selecting the reconstruction slice: for each respective attenuation image, back-projecting each pixel in the respective attenuation image back towards the respective emitter for that attenuation image onto the reconstruction slice and determining a proportion of overlap of that back-projected pixel with each grid cell to obtain a plurality of weighting factors comprising a respective weighting factor for each grid cell for that back-projected pixel; using the plurality of weighting factors for each back-projected pixel in each attenuation image to calculate an average back-projected intensity for each grid cell in the selected reconstruction slice to produce an average intensity image for the selected reconstruction slice; and convolving the average intensity image with a ramp filter to obtain the density function within the selected reconstruction slice.

BRIEF DESCRIPTION OF THE DRAWINGS

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

DETAILED DESCRIPTION

Figure 1:
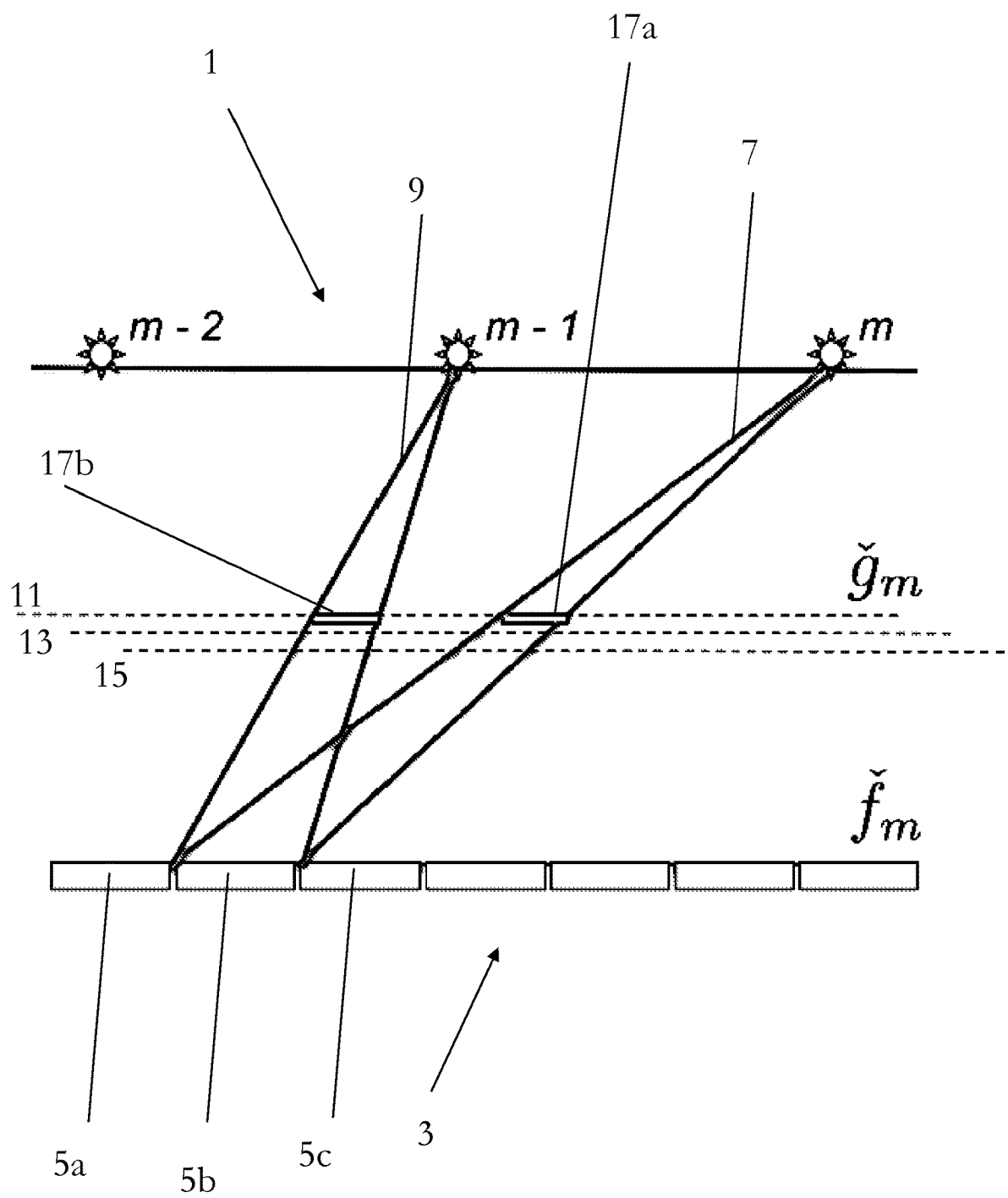
FIG. 1 is a side view of the geometry of the back-projection.

The present invention will be described with respect to certain drawings but the invention is not limited thereto but only by the claims. The drawings described are only schematic and are non-limiting. Each drawing may not include all of the features of the invention and therefore should not necessarily be considered to be an embodiment of the invention. In the drawings, the size of some of the elements may be exaggerated and not drawn to scale for illustrative purposes. The dimensions and the relative dimensions do not correspond to actual reductions to practice of the invention.

Furthermore, the terms first, second, third and the like in the description and in the claims, are used for distinguishing between similar elements and not necessarily for describing a sequence, either temporally, spatially, in ranking or in any other manner. It is to be understood that the terms so used are interchangeable under appropriate circumstances and that operation is capable in other sequences than described or illustrated herein. Likewise, method steps described or claimed in a particular sequence may be understood to operate in a different sequence.

Moreover, the terms top, bottom, over, under and the like in the description and the claims are used for descriptive purposes and not necessarily for describing relative positions. It is to be understood that the terms so used are interchangeable under appropriate circumstances and that operation is capable in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Similarly, it is to be noticed that the term "connected", used in the description, should not be interpreted as being restricted to direct connections only. Thus, the scope of the expression "a device A connected to a device B" should not be limited to devices or systems wherein an output of device A is directly connected to an input of device B. It means that there exists a path between an output of A and an input of B which may be a path including other devices or means. "Connected" may mean that two or more elements are either in direct physical or electrical contact, or that two or more elements are not in direct contact with each other but yet still co-operate or interact with each other. For instance, wireless connectivity is contemplated.

Reference throughout this specification to "an embodiment" or "an aspect" means that a particular feature, structure or characteristic described in connection with the embodiment or aspect is included in at least one embodiment or aspect of the present invention. Thus, appearances of the phrases "in one embodiment", "in an embodiment", or "in an aspect" in various places throughout this specification are not necessarily all referring to the same embodiment or aspect, but may refer to different embodiments or aspects. Furthermore, the particular features, structures or characteristics of any one embodiment or aspect of the invention may be combined in any suitable manner with any other particular feature, structure or characteristic of another embodiment or aspect of the invention, as would be apparent to one of ordinary skill in the art from this disclosure, in one or more embodiments or aspects.

Similarly, it should be appreciated that in the description various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Moreover, the description of any individual drawing or aspect should not necessarily be considered to be an embodiment of the invention. Rather, as the following claims reflect, inventive aspects lie in fewer than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some features included in other embodiments, combinations of features of different embodiments are meant to be within the scope of the invention, and form yet further embodiments, as will be understood by those skilled in the art. For example, in the following claims, any of the claimed embodiments can be used in any combination.

In the description provided herein, numerous specific details are set forth. However, it is understood that embodiments of the invention may be practised without these specific details. In other instances, well-known methods, structures and techniques have not been shown in detail in order not to obscure an understanding of this description.

In the discussion of the invention, unless stated to the contrary, the disclosure of alternative values for the upper or lower limit of the permitted range of a parameter, coupled with an indication that one of said values is more highly preferred than the other, is to be construed as an implied statement that each intermediate value of said parameter, lying between the more preferred and the less preferred of said alternatives, is itself preferred to said less preferred value and also to each value lying between said less preferred value and said intermediate value.

The use of the term "at least one" may mean only one in certain circumstances. The use of the term "any" may mean "all" and/or "each" in certain circumstances.

The principles of the invention will now be described by a detailed description of at least one drawing relating to exemplary features. It is clear that other arrangements can be configured according to the knowledge of persons skilled in the art without departing from the underlying concept or technical teaching, the invention being limited only by the terms of the appended claims.

FIG. 1 is a side view of the geometry of the back-projection in which an emitter panel 1 is located over a detector panel 3. The emitter panel 1 comprises a plurality of emitters (m, m−1, m−2). The detector panel 3 comprises a plurality of pixels 5. For each attenuation image $\check{f}_{in}$ (produced by the emitter m), rays are traced back from each pixel to the emitter m. For example, for the attenuation image $\check{f}_{in}$ (produced by the emitter m), rays 7 are traced back from the pixel 5b to the emitter m, and for the attenuation image $\check{f}_{m-1}$ (produced by the emitter m−1), rays 9 are traced back from the pixel 5b to the emitter m−1.

These rays 7, 9 intersect various reconstruction planes 11, 13, 15 located between the emitter panel 1 and detector panel 3 and shown parallel thereto in the figure (but this is not necessarily the case in alternative embodiments). In this way, the pixel 5b may be projected onto these planes, for example onto plane 11 at region 17a for emitter m, and at region 17b for emitter m−1.

For each emitter m, the back-projected image in the chosen reconstruction plane 11 can then be determined as $\check{g}_m$.

Figure 2:
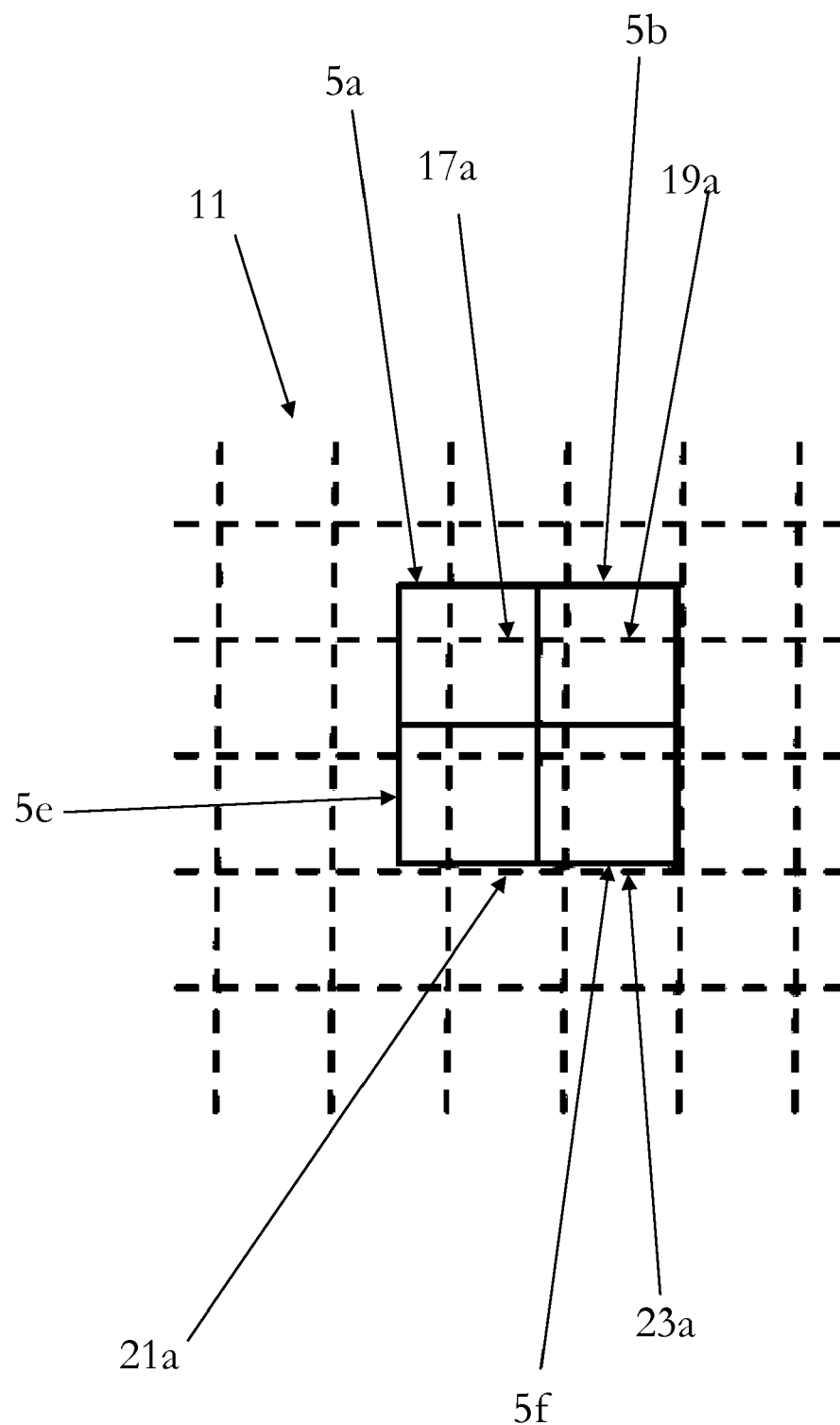
FIG. 2 is a plan view of pixels projected onto the grid cells.

FIG. 2 is a plan view of pixels 5a and 5b of FIG. 1 (and additional adjacent pixels 5e and 5f) projected onto the grid cells of plane 11 for a single emitter m, as regions 17a, 19a, 21a and 23a, respectively.

Figure 3:
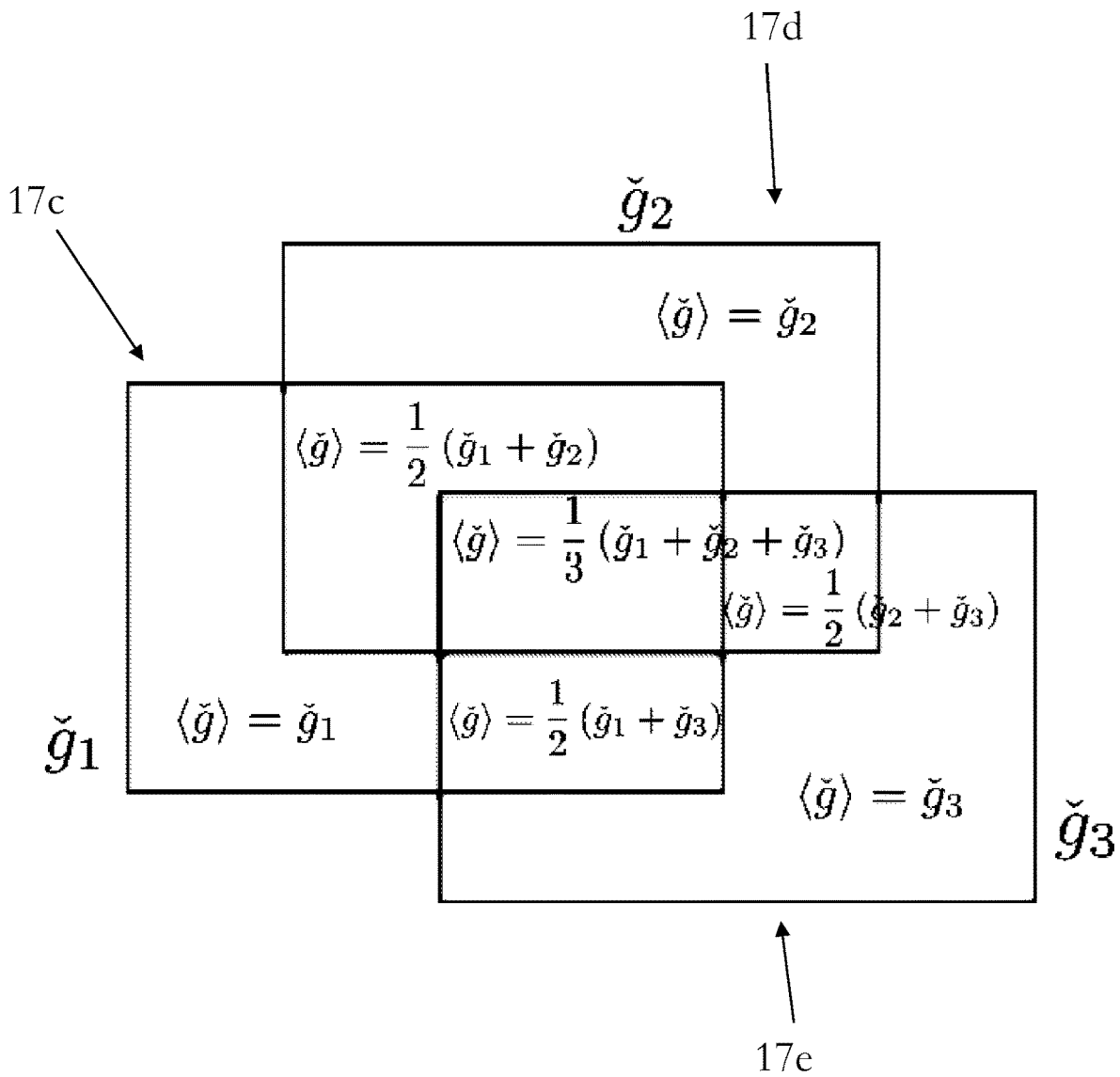
FIG. 3 is an example of the determination of average intensities once weighting factors have been applied.

FIG. 3 is an example of the determination of average intensities $\langle \check{g} \rangle$ in a plane 11 for back-projected pixel regions 17c, 17d, 17e from emitters m=1, m=2 and m=3, respectively, once weighting factors have been applied.

The invention claimed is:

1. A method of producing a tomogram, the method comprising the steps of:
providing an x-ray detector panel comprising a plurality of pixels;
providing an x-ray emitter panel spaced from the x-ray detector panel, the emitter panel comprising a plurality of x-ray emitters;
identifying relative locations of the emitters and pixels relative to each other;
emitting a respective cone of x-ray radiation from each emitter toward the detector panel;
producing respective attenuation images at the detector panel in response to each respective cone of x-ray radiation impinging the detector panel; and
reconstructing a density function indicative of attenuation of the x-ray radiation by:
selecting a reconstruction slice corresponding to a plane located between the detector and emitter panels;
providing an array of grid cells on the reconstruction slice;
in response to selecting the reconstruction slice: for each respective attenuation image, back-projecting each pixel in the respective attenuation image back towards the respective emitter for that attenuation image onto the reconstruction slice and determining a proportion of overlap of that back-projected pixel with each grid cell to obtain a plurality of weighting factors comprising a respective weighting factor for each grid cell for that back-projected pixel;
using the plurality of weighting factors for each back-projected pixel in each attenuation image to calculate an average back-projected intensity for each grid cell in the selected reconstruction slice to produce an average intensity image for the selected reconstruction slice; and
convolving the average intensity image with a ramp filter to obtain the density function within the selected reconstruction slice.

2. A system for producing a tomogram, the system comprising:
an x-ray emitter panel comprising a plurality of x-ray emitters, each emitter configured to emit a respective cone of x-ray radiation;
an x-ray detector panel comprising a plurality of pixels, the x-ray detector panel spaced from the x-ray emitter panel and configured to produce respective attenuation images in response to each respective cone of x-ray radiation impinging the detector panel from the x-ray emitter panel;
a spatial location system for identifying relative locations of the emitters and pixels relative to each other; and
a processor for reconstructing a density function indicative of attenuation of the x-ray radiation by:
selecting a reconstruction slice corresponding to a plane located between the detector and emitter panels;
providing an array of grid cells on the reconstruction slice;
in response to selecting the reconstruction slice: for each respective attenuation image, back-projecting each pixel in the respective attenuation image back towards the respective emitter for that attenuation image onto the reconstruction slice and determining a proportion of overlap of that back-projected pixel with each grid cell to obtain a plurality of weighting factors comprising a respective weighting factor for each grid cell for that back-projected pixel;

using the plurality of weighting factors for each back-projected pixel in each attenuation image to calculate an average back-projected intensity for each grid cell in the selected reconstruction slice to produce an average intensity image for the selected reconstruction slice; and convolving the average intensity image with a ramp filter to obtain the density function within the selected reconstruction slice.

* * * * *